US010458895B2

(12) United States Patent
Madabhushi et al.

(10) Patent No.: US 10,458,895 B2
(45) Date of Patent: Oct. 29, 2019

(54) PREDICTING RESPONSE TO PEMETREXED CHEMOTHERAPY IN NON-SMALL CELL LUNG CANCER (NSCLC) WITH BASELINE COMPUTED TOMOGRAPHY (CT) SHAPE AND TEXTURE FEATURES

(71) Applicant: Case Western Reserve University, Cleveland, OH (US)

(72) Inventors: Anant Madabhushi, Shaker Heights, OH (US); Vamsidhar Velcheti, Pepper Pike, OH (US); Mahdi Orooji, Cleveland, OH (US); Sagar Rakshit, Gurgaon (IN); Mehdi Alilou, Cleveland, OH (US); Niha Beig, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 221 days.

(21) Appl. No.: 15/612,467

(22) Filed: Jun. 2, 2017

(65) Prior Publication Data

US 2017/0351939 A1 Dec. 7, 2017

Related U.S. Application Data

(60) Provisional application No. 62/345,960, filed on Jun. 6, 2016.

(51) Int. Cl.
*G01N 15/14* (2006.01)
*G06T 7/11* (2017.01)
(Continued)

(52) U.S. Cl.
CPC ......... *G01N 15/14* (2013.01); *G01N 15/1475* (2013.01); *G06K 9/6256* (2013.01);
(Continued)

(58) Field of Classification Search
CPC ................ G06K 9/6267; G06T 7/0012; G06T 2207/30064
See application file for complete search history.

(56) References Cited

U.S. PATENT DOCUMENTS 9,208,556 B2 * 12/2015 Giger ................... G06K 9/6253
2004/0013292 A1 * 1/2004 Raunig ................ G06K 9/0014
382/128

(Continued)

*Primary Examiner* — Nay A Maung
*Assistant Examiner* — Jose Torres
(74) *Attorney, Agent, or Firm* — Eschweiler & Potashnik, LLC

(57) ABSTRACT

Methods, apparatus, and other embodiments predict response to pemetrexed based chemotherapy. One example apparatus includes an image acquisition circuit that acquires a radiological image of a region of tissue demonstrating NSCLC that includes a region of interest (ROI) defining a tumoral volume, a peritumoral volume definition circuit that defines a peritumoral volume based on the boundary of the ROI and a distance, a feature extraction circuit that extracts a set of discriminative tumoral features from the tumoral volume, and a set of discriminative peritumoral features from the peritumoral volume, and a classification circuit that classifies the ROI as a responder or a non-responder using a machine learning classifier based, at least in part, on the set of discriminative tumoral features and the set of discriminative peritumoral features.

17 Claims, 11 Drawing Sheets

(51) Int. Cl.
*G06K 9/62* (2006.01)
*G06T 7/00* (2017.01)
*A61B 6/00* (2006.01)
*G01N 33/483* (2006.01)
*A61B 6/03* (2006.01)
*G06K 9/32* (2006.01)
*G06K 9/46* (2006.01)

(52) U.S. Cl.
CPC .......... *G06K 9/6267* (2013.01); *G06T 7/0012* (2013.01); *G06T 7/0014* (2013.01); *G06T 7/11* (2017.01); *A61B 6/03* (2013.01); *A61B 6/466* (2013.01); *G01N 33/4833* (2013.01); *G06K 9/3233* (2013.01); *G06K 9/4642* (2013.01); *G06K 2209/053* (2013.01); *G06T 2207/10081* (2013.01); *G06T 2207/20081* (2013.01); *G06T 2207/30061* (2013.01); *G06T 2207/30064* (2013.01); *G06T 2207/30096* (2013.01)

(56) References Cited

U.S. PATENT DOCUMENTS

| | | | | |
|---|---|---|---|---|
| 2009/0234237 A1* | 9/2009 | Ross | ............ | A61B 5/026 600/504 |
| 2014/0301619 A1* | 10/2014 | Stavros | ............ | A61B 8/0825 382/131 |
| 2016/0203599 A1* | 7/2016 | Gillies | ............ | A61B 6/463 382/132 |

* cited by examiner

PREDICTING RESPONSE TO PEMETREXED CHEMOTHERAPY IN NON-SMALL CELL LUNG CANCER (NSCLC) WITH BASELINE COMPUTED TOMOGRAPHY (CT) SHAPE AND TEXTURE FEATURES

CROSS REFERENCE TO RELATED APPLICATIONS

This application claims the benefit of U.S. Provisional Application 62/345,960 filed Jun. 6, 2016.

FEDERAL FUNDING NOTICE

This invention was made with government support under grants CA208236, CA167811, DK098503, CA179327, CA195152, CA199374, and CA202752 awarded by the National Institutes of Health, and under grants W81XWH-13-1-0418, W81XWH-14-1-0323, W81XWH-15-1-0613, W81XWH-16-1-0329 awarded by the Department of Defense. The government has certain rights in the invention.

BACKGROUND

Pemetrexed is approved as a monotherapy for second line and maintenance treatment of non-squamous non-small cell lung cancer. (NSCLC) Pemetrexed based platinum doublet chemotherapy followed by maintenance pemetrexed chemotherapy is the current standard of care for lung adenocarcinoma with no actionable mutations. However, many patients receiving such cytotoxic chemotherapy do not receive clinical benefit from the therapy.

Response rate to pemetrexed based regimes as initial treatment is approximately 24-31%, while the disease control rate is approximately 60%. Response rate to pemetrexed is approximately 11.5% in the second line setting. Currently no clinically validated predictive marker is available to identify which patients will benefit from pemetrexed treatment. Thus, since pemetrexed treatment is expensive and may have significant side effects, it would be beneficial to more accurately determine which patients are more likely to benefit from pemetrexed treatment.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Pemetrexed based platinum doublet chemotherapy followed by maintenance pemetrexed for lung adenocarcinoma is the standard of care for NSCLC patients with no actionable mutations. Pemetrexed is also approved as monotherapy for second line maintenance treatment of non-squamous NSCLC. However, many patients receiving such cytotoxic chemotherapy do not receive clinical benefit from the treatment. The response rate to pemetrexed based regimens as initial treatment is approximately 24-31%, while the disease control rate is approximately 60%. If a cancer keeps growing or returns after one kind of treatment, it may be possible that another treatment plan may cure the cancer, or keep it under control. However, when a patient has been subjected to different treatments and no longer demonstrates improvements, even newer treatments may no longer be useful, and may therefore just be an expensive waste of time. Thus, differentiating responders from non-responders to pemetrexed therapy is a significant challenge faced by radiologists. Currently there are no clinically validated biomarkers to identify patients who will benefit from pemetrexed chemotherapy. Conventional approaches to predicting benefit from pemetrexed chemotherapy provide no better results than guessing.

Example methods and apparatus predict clinical benefit and treatment response for pemetrexed based chemotherapy in NSCLC patients using texture and shape features extracted from tumoral and peritumoral regions of tissue represented in computed tomography (CT) images. A peritumoral region may be defined as the region surrounding the tumoral region out to a distance. For example, in one embodiment, the peritumoral region may be the region extending 2.5 mm from the tumoral boundary. In another embodiment, the peritumoral region may be the region extending 5 mm from the tumoral boundary. The peritumoral region may be defined by a distance measured in mm, as described, or in other units, including pixels.

Figure 11:
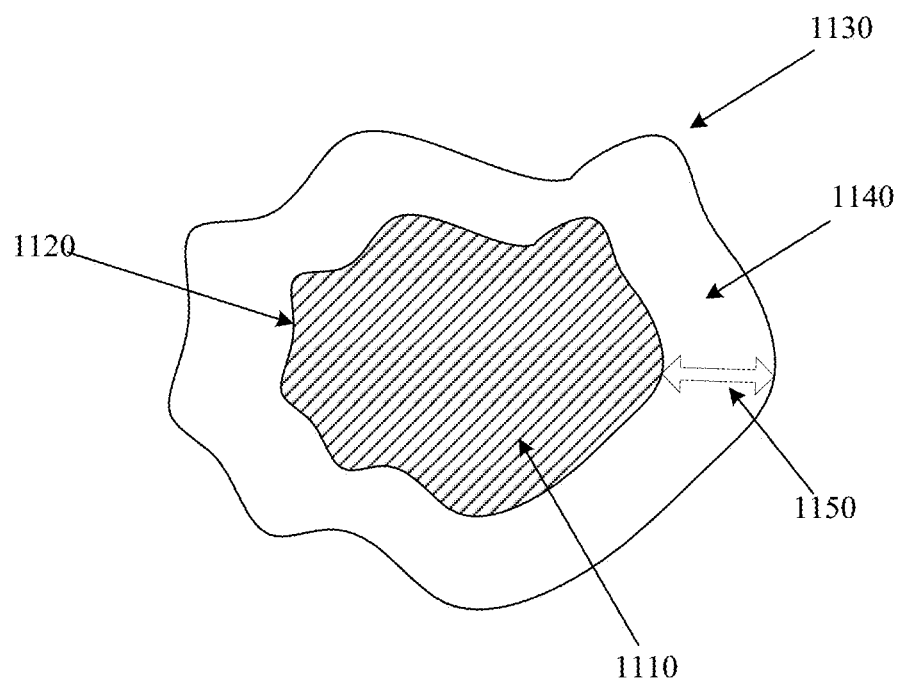
FIG. 11 illustrates an example peritumoral volume.

FIG. 11 illustrates an example peritumoral region 1140 associated with an NSCLC tumor 1110. Peritumoral region 1140 is bounded by outer peritumoral boundary 1130 and tumoral boundary 1120. In one embodiment, example methods and apparatus morphologically dilate tumoral boundary 1110 by an amount 1150, resulting in the outer peritumoral boundary 1130. Amount 1150 may be, for example, 2.5 mm, 5 mm, 7 pixels, or another, different amount.

In another embodiment, the peritumoral boundary may be generated using other techniques. For example, the peritumoral boundary may be defined as a function of a property of the tumor. The property of the tumor may include, for example, a diameter, a radius, a perimeter, an area, a volume, or other property of the tumor. The function may define the peritumoral region as, for example, a morphologic dilation of the tumoral boundary, where the dilation ratio is defined by a magnitude of an axis of the tumor. In another embodiment, the peritumoral boundary may be defined as a disc of a threshold radius defined about the centroid of the tumor, or defined on the focal points of an elliptical representation of the tumor. In one embodiment, the peritumoral boundary may be manually defined. Other approaches or combinations of approaches may be used to define the peritumoral boundary.

Example methods and apparatus extract quantitative image descriptors from radiological images to generate predictive and prognostic information, and thus provide non-invasive biomarkers for disease prognosis and personalized treatment planning. Example methods and apparatus predict clinical benefit or response to pemetrexed chemotherapy with an accuracy of at least 0.76 area under the receiver operating characteristic (ROC) curve (AUC).

In one embodiment, a database of pre-treatment CT images of advanced non-squamous NSCLC patients who were later treated with pemetrexed monotherapy is used. Patients are grouped into responders and non-responders. In this embodiment, a responder is defined as a patient who experienced complete or partial response, or stable disease for >=twelve cycles, and a non-responder is defined as a patient who experienced a best response of progressive disease and <=four cycles. A responder is labeled as a "1" and a non-responder is labeled as a "0". In this example, forty-six responders and forty-five non-responders are identified using this definition of responder and non-responder. Members of a set of CT images of the patients prior to initiation of pemetrexed are annotated on three dimensional (3D) slicer software. Annotating the images includes defining a region of interest (ROI) that defines a tumoral volume across slices. Annotating the image may also include defining a peritumoral region based on the boundary of the tumoral volume. The CT images are adjusted for image quality and are subjected to CT filters. After filtering and adjusting for image quality, twenty-six responders and twenty-seven non-responders remained and were used to form a training cohort or training set of images. A set of validation images was generated from images of patients distinct from the training cohort. Twenty-two responders and twenty-eight non-responders were included in the set of validation images. Texture features based on models applied to the distribution of Hounsfield units (HU) across pixels in the ROI are extracted from the image. Shape features based on the 3D distribution of boundary pixels are also acquired. Radiomic features are then extracted from both the tumoral region and the peritumoral region.

The discriminative property of the extracted radiomic features with respect to responders and non-responders in both the training set and the validation set is evaluated, in this example, using seven different machine learning classifiers and four different feature selection methods. The discriminative performance of the features and classifier is assessed using an area under the curve (AUC) of the receiver operating characteristic curve (ROC). In this example, an AUC of 1 indicates perfect discrimination, while an AUC of 0.5 indicates random guessing or no discrimination. An AUC of less than 0.5 indicates negative predictive ability worse than random guessing.

In this example, 1542 radiomic features were extracted from the tumoral and peritumoral volumes represented in the CT images. Four different feature selection approaches were used to reduce the redundancy of the radiomic features and to select the most discriminative and predictive features. In this example, a T-test feature selection approach, a Wilcoxon feature selection approach, a minimum redundancy maximum relevance (MRMR) approach, and a feed forward (FF) feature selection approach were employed. These feature selection approaches are filter approaches that rank the features using a scoring measure with different statistical tests. The higher the rank, the more discriminative the feature. By employing four different feature selection approaches and seven different classifiers, example methods and apparatus facilitate selecting the most discriminative combination of features and classifier.

In this example, consensus clustering is employed to provide quantitative evidence for determining the number of and affiliation of possible clusters within a dataset (e.g. the training cohort). To perform consensus clustering, the similarity between different nodules (e.g. tumors) based on distance in the space of the top ranked features is determined. Nodules belonging to different clusters have minimal correlation while nodules within a cluster have a high intra-class correlation.

Figure 4:
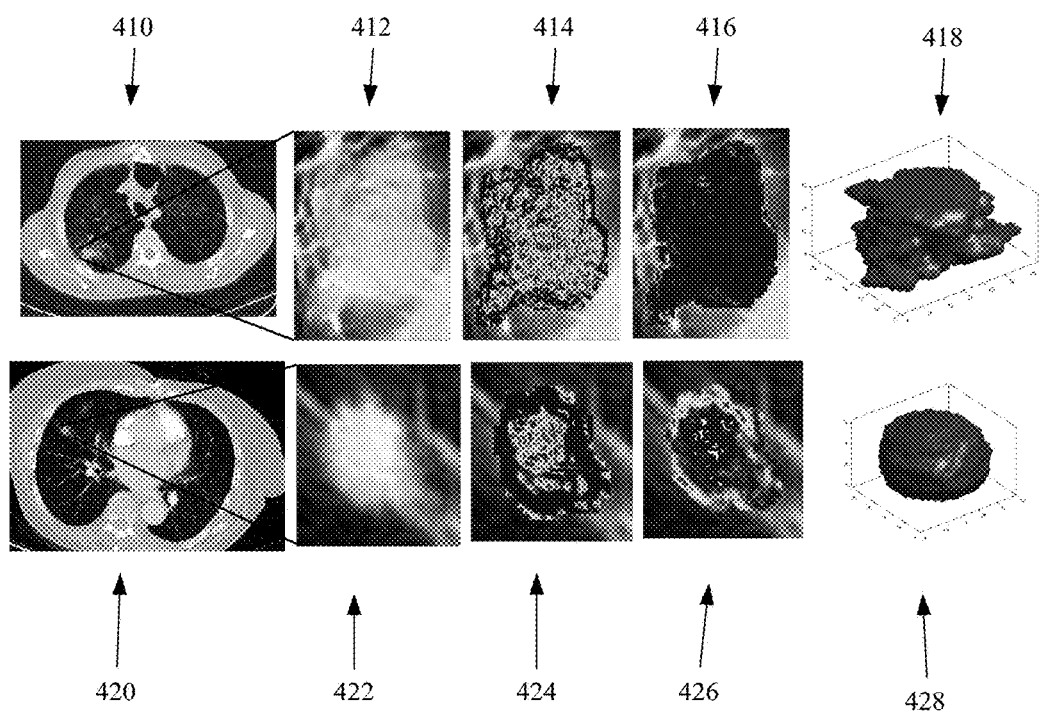
FIG. 4 illustrates example discriminative tumoral and peritumoral radiomic features identified on a responder and a non-responder to pemetrexed chemotherapy.

FIG. 4 illustrates example discriminative tumoral and peritumoral radiomic features identified on pre-treatment CT images of a responder and a non-responder. From an original CT image of a non-responder 410, a tumor region is annotated and represented as an annotated tumor 412. An energy texture feature is illustrated at 414, and a difference variance texture feature is illustrated at 416. A sphericity shape feature for the non-responder is illustrated at 418. An original CT image of a responder 420 has a tumor region annotated and represented as an annotated tumor 422. An energy texture feature is illustrated at 424, and a difference variance texture feature is illustrated at 426. A sphericity shape feature for the responder is illustrated at 428.

Figure 5:
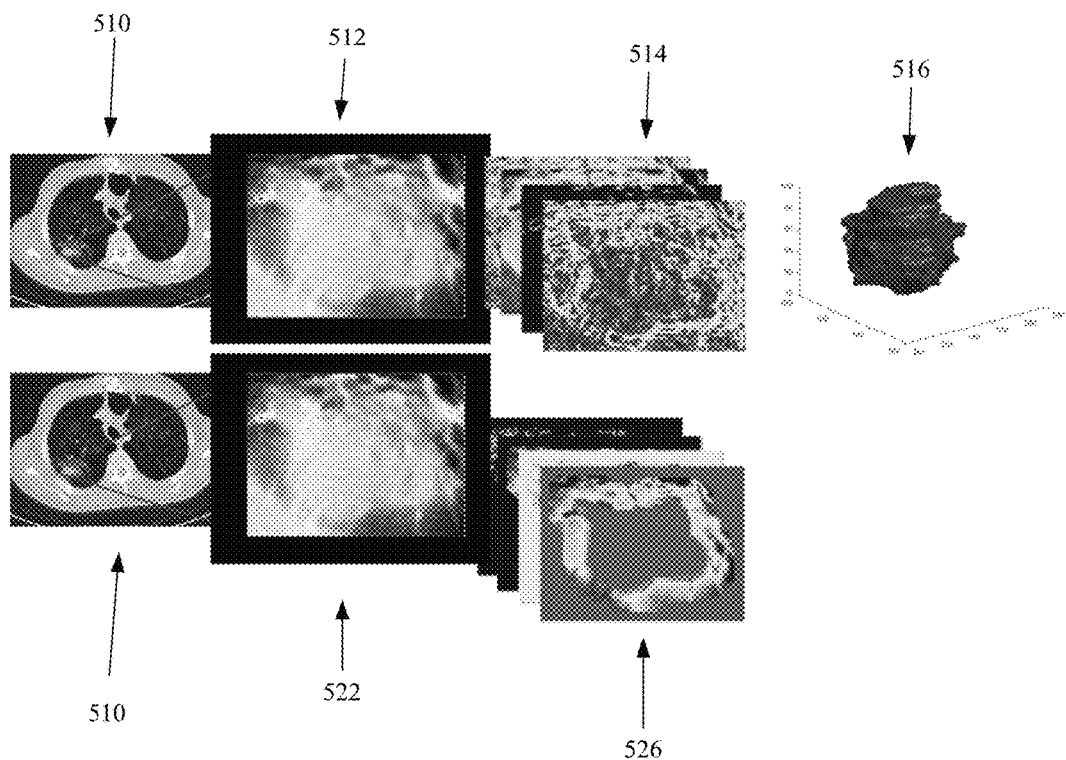
FIG. 5 illustrates example discriminative tumor and peritumoral radiomic features.

FIG. 5 illustrates example discriminative tumor and peritumoral radiomic features extracted from pre-treatment CT images of a region of tissue demonstrating NSCLC. From a CT image 510, an ROI of a tumor 512 is defined. Texture features 514 are extracted from the tumoral region. A shape feature 516 is also extracted. A peritumoral region 522 is also defined from the CT image 510. A texture feature 524 is extracted from the peritumoral region. Note that radiomic features extracted from a CT image by example methods and apparatus are sub-visual features that are not visible to the human eye. For example, while the tumoral ROIs represented by 412, 422, 512, and 522 demonstrate a homogeneity of HU between responders and non-responders, the extracted discriminative features demonstrate an informative heterogeneity that is sub-visual.

By increasing the accuracy with which clinical benefit or response to pemetrexed chemotherapy is predicted, example methods and apparatus produce the concrete, real-world technical effect of reducing the amount of unnecessary or non-beneficial pemetrexed chemotherapy administered to patients who are unlikely to benefit from the treatment. Additionally, example apparatus and methods reduce the expenditure of time, money and therapeutic resources on patients who are unlikely to benefit from the treatment. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
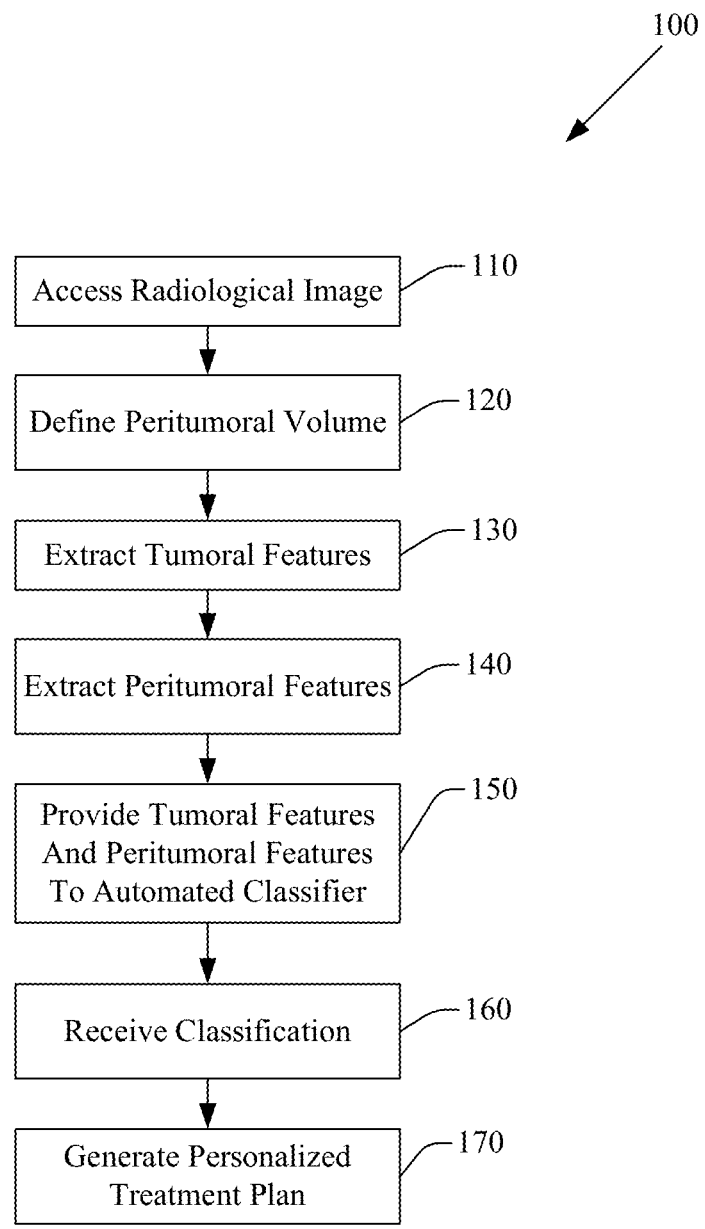
FIG. 1 illustrates an example computerized method for predicting response to pemetrexed chemotherapy.

FIG. 1 illustrates an example method 100 for predicting response to pemetrexed chemotherapy. Method 100 includes, at 110, accessing a pre-chemotherapy treatment radiological image of a region of tissue demonstrating cancerous pathology. The radiological image includes a plurality of pixels. The radiological image includes an annotated region of interest (ROI) that defines a tumoral volume. The tumoral region may be defined by or include a boundary. For example, in one embodiment, the ROI that defines the tumoral volume may be annotated on 3D slicer software by an expert radiologist. The ROI may be segmented across contiguous slices. In another embodiment, the tumoral volume may be automatically segmented. In one embodiment, the radiological image is a computed tomography (CT) image of a region of tissue demonstrating metastatic lung adenocarcinoma acquired before the patient represented in the radiological image has been subjected to pemetrexed based chemotherapy. In another embodiment, the radiological image may be acquired using different imaging techniques, or may be an image of a region of tissue demonstrating a different pathology, including different types of cancer. The radiological image has a slice thickness.

Accessing the radiological image may include retrieving electronic data from a computer memory, receiving a computer file over a computer network, or other computer or electronic based action. In one embodiment, the radiological image is acquired using a CT system. In another embodiment, other types or sizes of images may be accessed. The radiological image includes a set of morphological features. The set of morphological features includes a texture feature, a shape feature, or an intensity feature. The set of morphological features may be extracted on a per-pixel basis, on a per-voxel basis, or using another approach.

Method 100 also includes, at 120, defining a peritumoral volume based on the boundary. In one embodiment, the peritumoral volume is defined by the tumoral volume boundary and a number of pixels. For example, the peritumoral volume may be defined as a region extending seven pixels from the tumor boundary. In another embodiment, the distance or number of pixels used to define the peritumoral volume may be determined heuristically. For example, the distance or number of pixels may be based on a resolution of the radiological image. In one embodiment, the peritumoral volume may be defined using a distance of 2.5 mm, 5 mm, or other distance, from the tumoral volume boundary.

Method 100 also includes, at 130, extracting a set of discriminative tumoral features from the tumoral volume. In one embodiment, the set of discriminative tumoral features includes a shape feature and a texture feature. For example, in this embodiment, the set of discriminative tumoral features includes a sphericity feature, a Gabor feature, and a Law-Laplace feature. In another embodiment, the set of discriminative tumoral features may include other, different features.

Method 100 also includes, at 140, extracting a set of discriminative peritumoral features from the peritumoral (i.e. outside the tumor) volume. In one embodiment, the set of discriminative peritumoral features includes a texture feature. For example, in this embodiment, the set of discriminative peritumoral features includes a mean of Law feature. In another embodiment, the set of discriminative peritumoral features may include other, different features. The set of discriminative tumoral features and the set of discriminative peritumoral features may include, for example, a Haralick texture feature, a Laws texture feature, a Laws-Laplacian feature, a Gabor feature, a Local Binary Pattern (LBP) feature, a histogram of oriented gradient (HOG) feature, a dynamic HOG (DHOG) feature, a co-occurrence of local anisotropic gradient orientation (Co-LiAGe) feature, or a 3D shape feature.

The level of discriminability of a radiomic feature may be a function of, in part, a slice thickness. In one embodiment, the set of discriminative tumoral features and the set of discriminative peritumoral features are selected based, at least in part, on the slice thickness. A set of discriminative features that is more discriminative for a particular slice thickness may be selected instead of a different set of discriminative features that is more discriminative for a different slice thickness. For example, upon determining that the slice thickness has a first value, a first set of discriminative tumoral features and a first set of discriminative peritumoral features may be extracted. In this example, a second, different set of discriminative tumoral features and a second, different set of discriminative peritumoral features may be extracted upon determining that the slice thickness has a second, different value. By selecting the set of discriminative tumoral features and the set of discriminative peritumoral features based, at least in part, on the slice thickness, embodiments described herein improve on conventional approaches by optimizing features selection across different slice thicknesses. Thus, a radiological image acquired at a first hospital by a first CT system with a first thickness may have an optimum set of discriminative features extracted based on the slice thickness, while a radiological image acquired at a second, different hospital by a second CT system with a second, different slice thickness may have a different optimum set of discriminative features. Embodiments described herein facilitate extracting the optimum set of features for such disparate images.

Method 100 also includes, at 150, providing the set of discriminative tumoral features and the set of discriminative peritumoral features to a machine learning classifier. Providing the set of discriminative tumoral features and the set of discriminative peritumoral features may include retrieving electronic data from a computer memory, receiving a computer file over a computer network, or other computer or electronic based action. In one embodiment, the machine learning classifier is a linear discriminant analysis (LDA) classifier, a quadratic discriminant analysis (QDA) classifier, a K-nearest neighbors (KNN) classifier, a random forest (RF) classifier, or a support vector machine (SVM) classifier. In another embodiment, the machine learning classifier may be another, different type of machine learning classifier.

Method 100 also includes, at 160, receiving, from the machine learning classifier, a classification of the region of tissue. The classification is based on the set of discriminative tumoral features and the set of discriminative peritumoral features. Receiving the classification may include retrieving electronic data from a computer memory, receiving a computer file over a computer network, or other computer or electronic based action. The classification may classify the ROI of the patient represented in the ROI as a responder or a non-responder. The classification may include a probability that the ROI or the patient is a responder or non-responder.

Method 100 further includes, at 170, generating a personalized treatment plan based, at least in part, on the classification. Generating the personalized treatment plan may include controlling a computer aided diagnosis (CADx) system or other system to generate a personalized treatment plan. Generating the personalized treatment plan may include generating a pemetrexed therapy schedule for a patient, generating a pemetrexed dosage for a patient, or other action.

Figure 2:
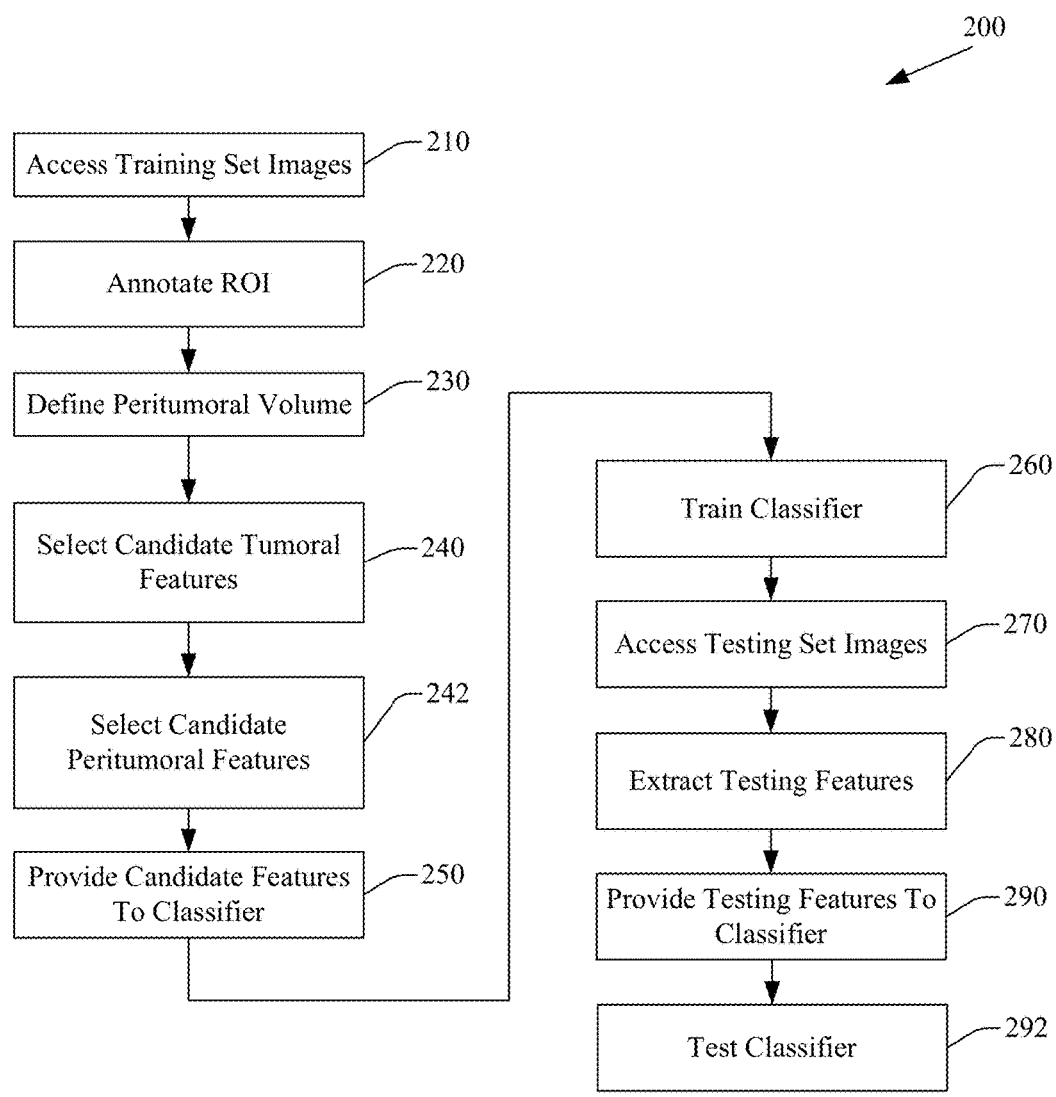
FIG. 2 illustrates an example computerized method for training a machine learning classifier to predict response to pemetrexed chemotherapy.

In one embodiment, method 100 may also include training the machine learning classifier. FIG. 2 illustrates an example method 200 of training a machine learning classifier. Method 200 includes, at 210 accessing a training set of radiological images. Accessing the training set of radiological images may include retrieving electronic data from a computer memory, receiving a computer file over a computer network, or other computer or electronic based action.

A member of the training set includes a plurality of pixels. The training set includes a radiological image of a region of tissue that responded to pemetrexed based chemotherapy, and a radiological image of a region of tissue that did not respond to pemetrexed based chemotherapy. A member of the training set may be, in one embodiment, a CT image. A member of the training set includes a set of radiomic features.

Method 200 also includes, at 220, annotating an ROI in the member of the training set. The ROI defines a tumoral volume. The tumoral volume includes a boundary. In one embodiment, the ROI that defines the tumoral volume may be annotated on 3D slicer software by an expert radiologist. The ROI may be segmented across contiguous slices. In another embodiment, the tumoral volume may be automatically segmented.

Method 200 also includes, at 230, defining a peritumoral volume based on the boundary. In one embodiment, the peritumoral volume is defined by the tumoral volume boundary and a number of pixels. For example, the peritumoral volume may be defined as a region extending seven pixels from the tumor boundary. In another embodiment, the distance or number of pixels used to define the peritumoral volume may be determined heuristically.

Method 200 also includes, at 240, selecting a first subset of candidate discriminative features from the tumoral volume.

Method 200 also includes, at 242, selecting a second, different subset of candidate discriminative features from the peritumoral volume. In one embodiment, the first subset of candidate discriminative features and the second, different subset of candidate discriminative features are selected using a T-Test approach, a Wilcoxon rank sum approach, a minimum redundancy maximum relevance (MRMR) approach, or a feed forward (FF) approach.

In one embodiment, the first subset of candidate discriminative features and the second, different subset of candidate discriminative features are selected from at least 1542 radiomic features extracted from the tumoral volume and the peritumoral volume of the member of the training set of radiological images. Radiomic features extracted by example methods and apparatus include texture features and shape features. The texture features and shape features may include a Haralick texture feature, a Laws texture feature, a Laws-Laplacian feature, a Gabor feature, a Local Binary Pattern (LBP) feature, a HOG feature, a DHOG feature, a CoLiAGe feature, or a 3D shape feature.

In one embodiment, Haralick texture features based on quantifying the spatial gray-level co-occurrence within local neighborhoods around a pixel in an image may be extracted. Haralick texture features are calculated from a tumoral volume or a peritumoral volume for an image by calculating six statistics (mean, median, variance, standard deviation, kurtosis and skewness) derived from the corresponding co-occurrence matrices.

In one embodiment, Laws Texture features are extracted after applying 5×5 separable symmetric or anti-symmetric masks for extracting level (L), edge (E), spot (S), wave (W), and ripple (R) patterns on an image. The convolution of these masks with the image give 25 distinct Laws feature representations. Thus, taking into account six statistics associated with the features, example methods and apparatus may extract, in this embodiment, 150 Law texture features from the tumoral or peritumoral region.

In one embodiment, Laws-Laplacian features are extracted from the tumoral or peritumoral region. Laws-Laplacian features involve convolving the original image with a Gaussian band pass filter. Then, a Laplacian is calculated by differentiating the original image from a low pass filtered image. In total, 150 Law-Laplacian features may be extracted.

In one embodiment, Gabor features are extracted from the tumoral or peritumoral region. Gabor filters have optimal localization properties in both spatial and frequency domains. A Gabor filter is a modulated sinusoidal complex plane of a particular frequency and orientation with a Gaussian envelope response and thus is well suited for texture segmentation problems. A total of 48 Gabor filters were constructed by tuning different frequencies and orientation and applied to images. In this embodiment, 288 Gabor features are extracted from an image.

In one embodiment, Local Binary Pattern (LBP) features and Dynamic local binary patterns (DLBP) features may be extracted. LBP features and DLPB features summarize the local structure in an image by comparing a pixel with other pixels in its neighborhood and generating a binary vector related to the intensity of the center pixels. The LBP process results in an 8-bit code-word describing the local neighborhood around a pixel. By combining the average cell histograms DLBP features are extracted. In this embodiment, ten LBP and DLBP features are extracted for an image.

In one embodiment, HOG and DHOG features may be extracted from the tumoral or peritumoral region. HOG features count occurrences of intensity gradient orientation in localized portions of an image. The image is divided into small connected cells and, for a cell, the number of occurrences of gradient directions are calculated. The combination of these histograms results in the HOG features. The dynamic version of the feature (DHOG) is calculated by applying the feature on an image sequence and averaging them across the multiple image frames. In this embodiment, twenty HOG and DHOG features were extracted.

In one embodiment, CoLIAGe features are extracted from the tumoral or peritumoral region. CoLIAGe features detect local anisotropic differences in voxel-level gradient orientations for distinguishing similar appearing phenotypes. CoLIAGe involves assigning an image voxel an entropy value associated with the co-occurrence matrix of gradient orientations computed around the voxel. In this embodiment, 78 CoLIAGe features were extracted.

In one embodiment, 3D shape features are extracted. Shape is an important visual feature of an ROI in the image. In one embodiment, convexity, width, height, depth, perimeter, area, eccentricity, compactness, radial distance, roughness, elongation equivalent diameter and 3D-sphericity of the ROI (e.g. tumor) are computed. Note that the width, height, depth as well as sphericity features are calculated in 3D space. The remaining features are computed in 2D on a slice by slice basis. The mean and standard deviation of a feature is computed across the pixels and over slices containing the tumor. In this embodiment, 24 shape features were extracted. In other embodiments, other, different features or numbers of features may be extracted.

Method 200 also includes, at 250, providing the first subset of candidate discriminative features and the second, different subset of candidate discriminative features to the machine learning classifier. Providing the first subset of candidate discriminative features and the second, different subset of candidate discriminative features may include retrieving electronic data from a computer memory, receiving a computer file over a computer network, or other computer or electronic based action.

Method 200 also includes, at 260, training the machine learning classifier. Training the machine learning classifier may include training the machine learning classifier using the first subset of candidate discriminative features and the second, different subset of candidate discriminative features.

Method 200 also includes, at 270, accessing a testing set of radiological images. Accessing the testing set may include retrieving electronic data from a computer memory, receiving a computer file over a computer network, or other computer or electronic based action. A member of the testing set includes a plurality of pixels. The testing set includes a pre-treatment radiological image of a region of tissue that responded to pemetrexed based chemotherapy, and a pre-treatment radiological image of a region of tissue that did not respond to pemetrexed based chemotherapy. A member of the testing set includes a set of features.

In one embodiment, method 200 may also include extracting a testing set of features from a member of the testing set of radiological images. The testing set includes the first subset of candidate discriminative features and the second, different subset of candidate discriminative features.

In one embodiment, method 200 may also include providing the testing set of features to the machine learning classifier. Providing the test set of features to the machine learning classifier may include retrieving electronic data from a computer memory, receiving a computer file over a computer network, or other computer or electronic based action.

Figure 3:
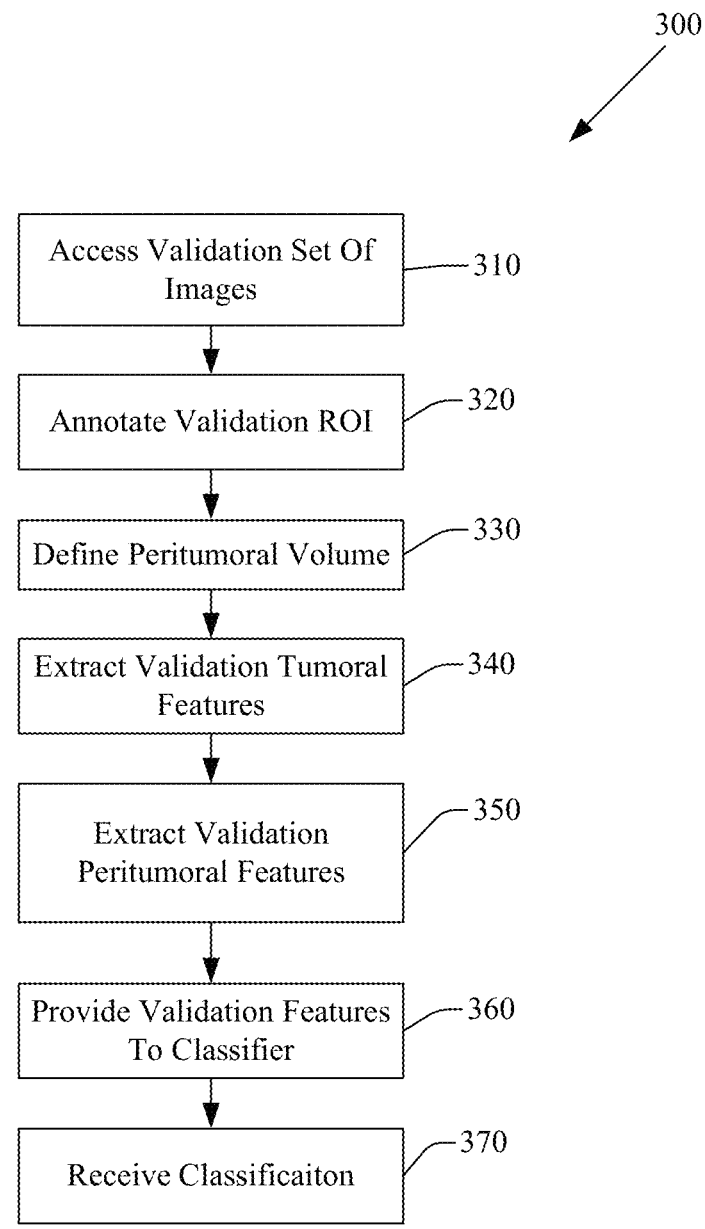
FIG. 3 illustrates an example computerized method for testing a machine learning classifier.

In one embodiment, method 200 may also include, at 292, testing the machine learning classifier. FIG. 3 illustrates an example method 300 for testing the machine learning classifier.

Method 300 includes, at 310 accessing an independent validation set of radiological images. Accessing the independent validation set of radiological images may include retrieving electronic data from a computer memory, receiving a computer file over a computer network, or other computer or electronic based action. A member of the independent validation set includes a plurality of pixels. The member of the independent validation set is a pre-treatment radiological image of a responder to pemetrexed based chemotherapy, or a pre-treatment radiological image of a non-responder to pemetrexed based chemotherapy. The member of the independent validation set may be CT image.

Method 300 also includes, at 320 annotating a validation ROI in the member of the independent validation set. The validation ROI defines a tumoral volume. The tumoral volume includes a boundary. In one embodiment, the ROI that defines the tumoral volume may be annotated on 3D slicer software by an expert radiologist. The ROI may be segmented across contiguous slices. In another embodiment, the tumoral volume may be automatically segmented.

Method 300 also includes, at 330, defining a peritumoral volume based on the boundary. In one embodiment, the peritumoral volume is defined by the tumoral volume boundary and a number of pixels. For example, the peritumoral volume may be defined as a region extending seven pixels from the tumor boundary. In another embodiment, the distance or number of pixels used to define the peritumoral volume may be determined heuristically.

Method 300 also includes, at 340, extracting a first validation set of features from the tumoral volume. Method 300 also includes, at 350, extracting a second validation set of features from the peritumoral volume. In one embodiment, the first validation set and the second validation set are based on the first subset of candidate discriminative features and the second, different subset of candidate discriminative features.

Method 300 also includes, at 360, providing the first validation set of features and the second validation set of features to the machine learning classifier. Providing the first validation set of features and the second validation set of features to the machine learning classifier may include retrieving electronic data from a computer memory, receiving a computer file over a computer network, or other computer or electronic based action.

Method 300 further includes, at 370, receiving, from the machine learning classifier, a classification of the validation ROI. The classification of the validation ROI is based, at least in part, on the first validation set of features and the second validation set of features.

Training the machine learning classifier and testing the machine learning classifier facilitates selecting an optimal set of discriminative features. For example, in one embodiment, using an MRMR feature selection approach, the four most discriminative features are "Standard Deviation of Gabor", "Skewness of Law-Laplace", "Variance of Law-Laplace" and "Median of Gabor" respectively. By using these four features and training classifiers with two third of patients in the training set and validating on one third of them on the same set, after averaging all over 1000 repetitions, the results for a KNN classifier, an LDA classifier, a QDA classifier, an SVM-Linear classifier, an SVM-RBF classifier, an SVM-Polynomial classifier, and a RF classifier are 76.10%, 72.73%, 72.93%, 71.50%, 77.53%, 52.35% and 78.49% respectively. In one embodiment using a T-test score (TSCR) feature selection approach, the most discriminative features are "Mean of Haralick", "kurtosis of Law-Laplace", "kurtosis of Law" and "Median of Haralick" respectively. In another embodiment, a Wilcoxon feature selection approach selects "Median of Haralick" and "Median of peritumoral Haralick" as the most discriminative features, while a FF feature selection approach selects "Median of Gabor", "Mean of Law" and "skewness of peritumoral Haralick" as the most discriminative four features respectively.

Figure 6:
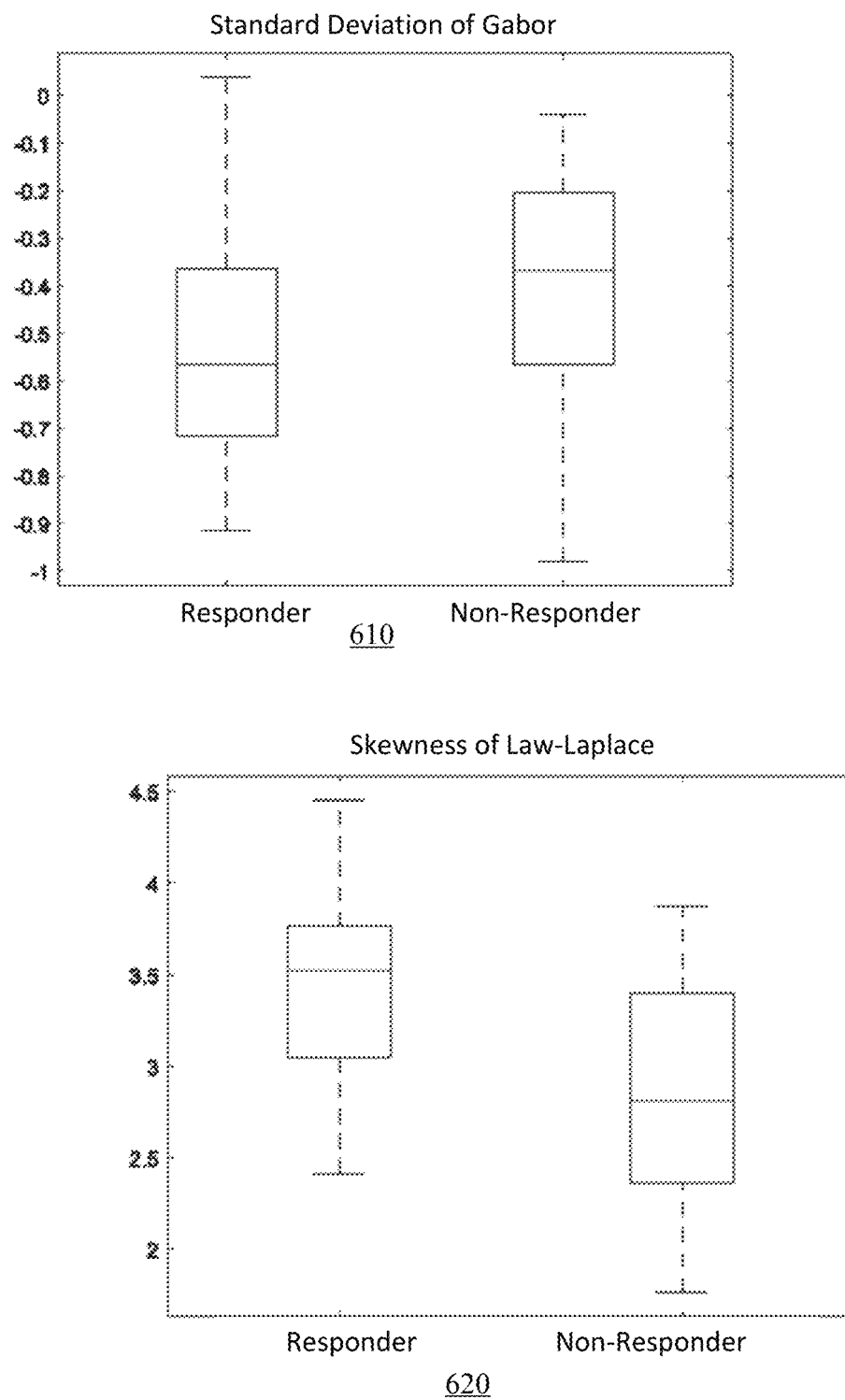
FIG. 6 illustrates box and whisker plots of discriminative features.

FIG. 6 illustrates box and whisker plots of discriminative features. Element 610 illustrates a box and whisker plot corresponding to the mean of the standard deviation of a Gabor texture feature extracted from tumoral volumes in a training set identified using an MRMR feature selection approach. Element 620 illustrates a box and whisker plot corresponding to the mean of the skewness of Law-Laplace texture features extracted from tumoral volumes in the training set identified using an MRMR feature selection approach.

While FIGS. 1, 2, 3, and 9 illustrate various actions occurring in serial, it is to be appreciated that various actions illustrated in FIG. 1, FIG. 2, FIG. 3, or FIG. 9 could occur substantially in parallel. By way of illustration, a first process could access a radiological image, a second process could define a peritumoral volume, and a third process could extract discriminative features. While three processes are described, it is to be appreciated that a greater or lesser number of processes could be employed and that lightweight processes, regular processes, threads, and other approaches could be employed.

Methods, apparatus, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the invention. In the figures, the thicknesses of lines, layers and/or regions may be exaggerated for clarity. Nothing in this detailed description (or drawings included herewith) is admitted as prior art.

Like numbers refer to like or similar elements throughout the description of the figures. When an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In one example, a method may be implemented as computer executable instructions. Thus, in one example, a computer-readable storage device may store computer executable instructions that if executed by a machine (e.g., computer, processor) cause the machine to perform methods described or claimed herein including method 100, method 200, method 300, and method 900. While executable instructions associated with the listed methods are described as being stored on a computer-readable storage device, it is to be appreciated that executable instructions associated with other example methods described or claimed herein may also be stored on a computer-readable storage device.

In different embodiments the example methods described herein may be triggered in different ways. In one embodiment, a method may be triggered manually by a user. In another example, a method may be triggered automatically.

Figure 7:
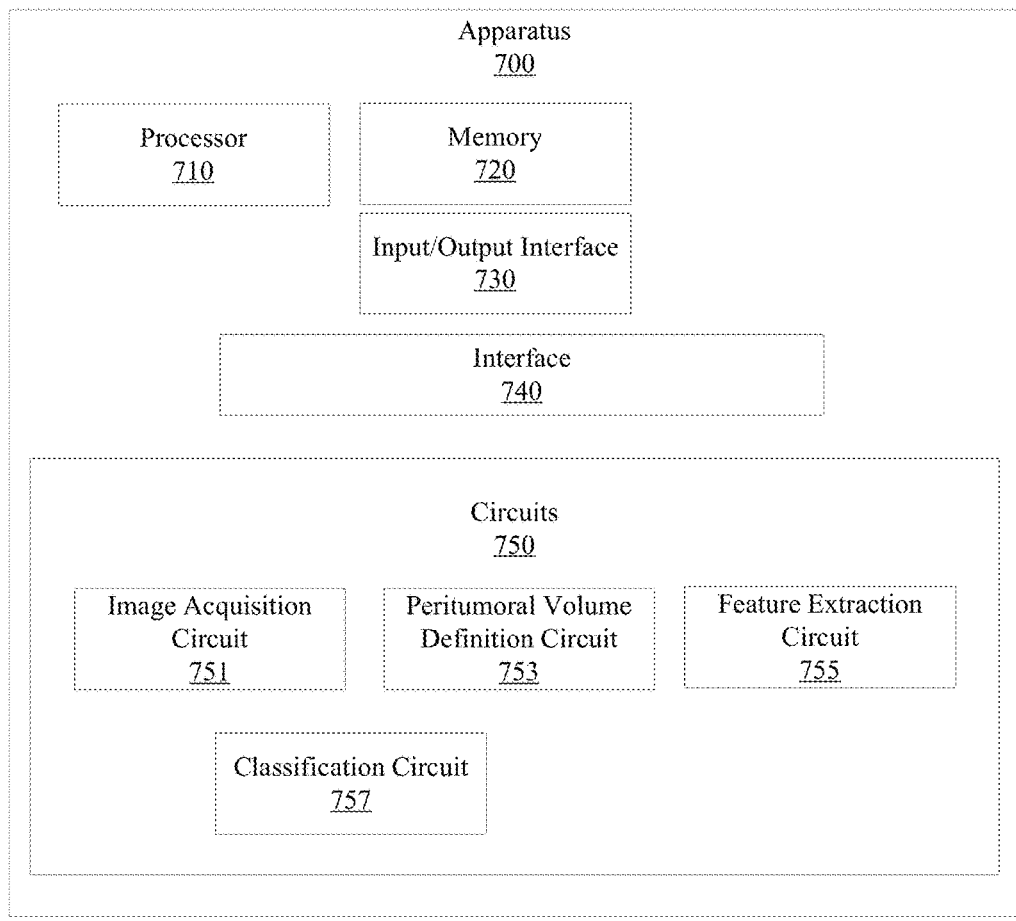
FIG. 7 illustrates an example apparatus for predicting response to pemetrexed chemotherapy.

FIG. 7 illustrates an example apparatus 700 for predicting response to pemetrexed therapy in NSCLC patients. Apparatus 700 includes a processor 710, a memory 720, an input/output (I/O) interface 730, a set of circuits 750, and an interface 740 that connects the processor 710, the memory 720, the I/O interface 730, and the set of circuits 750. The set of circuits 750 includes an image acquisition circuit 751, a peritumoral volume definition circuit 753, a feature extraction circuit 755, and a classification circuit 757. In one embodiment, the functionality associated with the set of circuits 750 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 750 are implemented as ASICs or SOCs.

Image acquisition circuit 751 acquires a radiological image of a region of tissue demonstrating NSCLC. The radiological image is a pre-pemetrexed treatment image of the region of tissue. The radiological image includes a plurality of pixels. The radiological image is a computed tomography (CT) image that has a slice thickness. The radiological image includes a region of interest (ROI) that defines a tumoral volume. The ROI has a boundary. In one embodiment, the ROI that defines the tumoral volume may be annotated on 3D slicer software by an expert radiologist. The ROI may be segmented across contiguous slices. In another embodiment, the tumoral volume may be automatically segmented. Other image modalities, dimensions, pixel sizes, or resolutions may also be used.

Peritumoral volume definition circuit 753 defines a peritumoral volume based, at least in part, on the boundary of the ROI and a distance. The distance is a number of pixels. In one embodiment the distance is heuristically determined. For example, the distance may be a function of an area defined by the ROI. In another embodiment, the distance is seven pixels. In another embodiment, other distances or approaches to selecting the distance or defining the peritumoral volume may be employed.

Feature extraction circuit 755 extracts a set of discriminative tumoral features from the tumoral volume. Feature extraction circuit 755 also extracts a set of discriminative peritumoral features from the peritumoral volume. In one embodiment, feature extraction circuit 755 extracts the set of discriminative tumoral features and the set of discriminative peritumoral features based, at least in part, on the slice thickness. The set of discriminative tumoral features includes a shape feature and a texture feature. The set of discriminative peritumoral features includes a texture feature.

Classification circuit 757 classifies the ROI as a responder or a non-responder using a machine learning classifier. Classification circuit 757 classifies the ROI based, at least in part, on the set of discriminative tumoral features and the set of discriminative peritumoral features. In one embodiment, the machine learning classifier is an LDA machine learning classifier. In another embodiment, classification circuit 757 classifies the ROI using a machine learning classifier selected from at least one of an LDA, a QDA classifier, a K-nearest neighbors (KNN) classifier, a random forest classifier, or an SVM classifier. Classification circuit 757 may select the machine learning classifier based, at least in part, on the slice thickness. Classification circuit 757 may classify the ROI or the patient from which the ROI was imaged as a responder or a non-responder. Classification circuit 757 may also compute a probability that the ROI will respond or not respond to pemetrexed therapy.

In one embodiment of apparatus 700, the set of circuits 750 also includes a display circuit. The display circuit may control a CADx system, a CT system, a personalized cancer treatment system, or computer to display the radiological image, the features, or the classification on a computer monitor, a smartphone display, a tablet display, or other displays. Displaying the image, the features, or the classification may also include printing the radiological image, the features, or the classification. The display circuit may also control the CADx system, personalized cancer treatment system, or computer to display an image of the region of tissue represented by the ROI. The image of the region of tissue may include an annotated image of the ROI, the peritumoral volume, or the features. By displaying the annotated image of the ROI, the peritumoral volume, or the features, example apparatus provide a timely and intuitive way for a human pathologist, a personalized cancer treatment system, or a CADx system to more accurately predict response to therapy, including pemetrexed based chemotherapy, thus improving on conventional approaches to predicting response to treatment.

Figure 8:
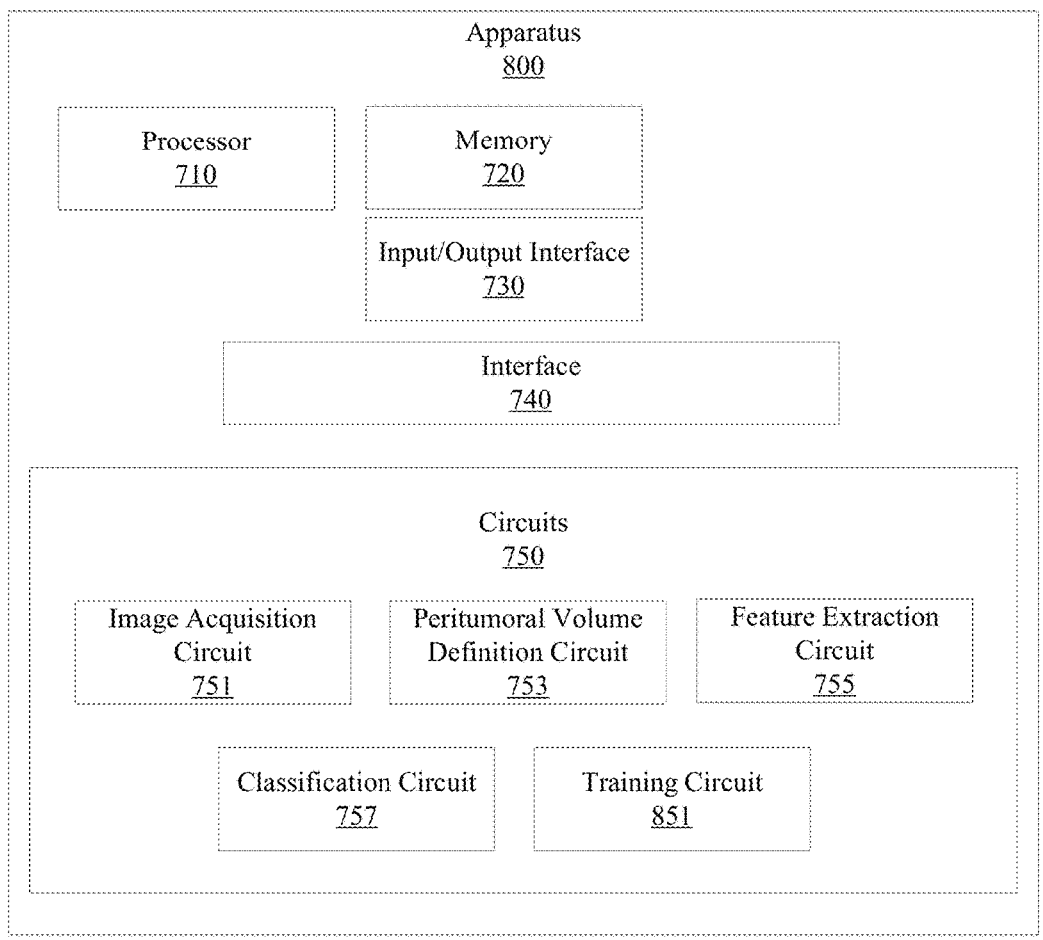
FIG. 8 illustrates an example apparatus for predicting response to pemetrexed chemotherapy.

FIG. 8 illustrates an example apparatus 800 that is similar to apparatus 700 but that includes additional elements and details. Apparatus 800 includes training circuit 851. Training circuit 851 trains the machine learning classifier using an independent learning set of radiological images and an independent testing set of radiological images. The independent learning set includes at least one pre-treatment image of a responder to pemetrexed therapy, and at least one pre-treatment image of a non-responder. The independent validation set includes at least one pre-treatment image of a responder to pemetrexed therapy, and at least one pre-treatment image of a non-responder. Training circuit 851 may control feature extraction circuit 755 to extract at least one different combinations of discriminative features from the independent learning set or the independent testing set, and to provide the at least one different combination of discriminative features to at least one of an LDA classifier, a QDA classifier, a KNN classifier, a random forest classifier, or an SVM classifier. Training circuit 851 may test the machine learning classifier using the independent testing set. The independent learning set and the independent testing set may be disjoint sets.

Figure 9:
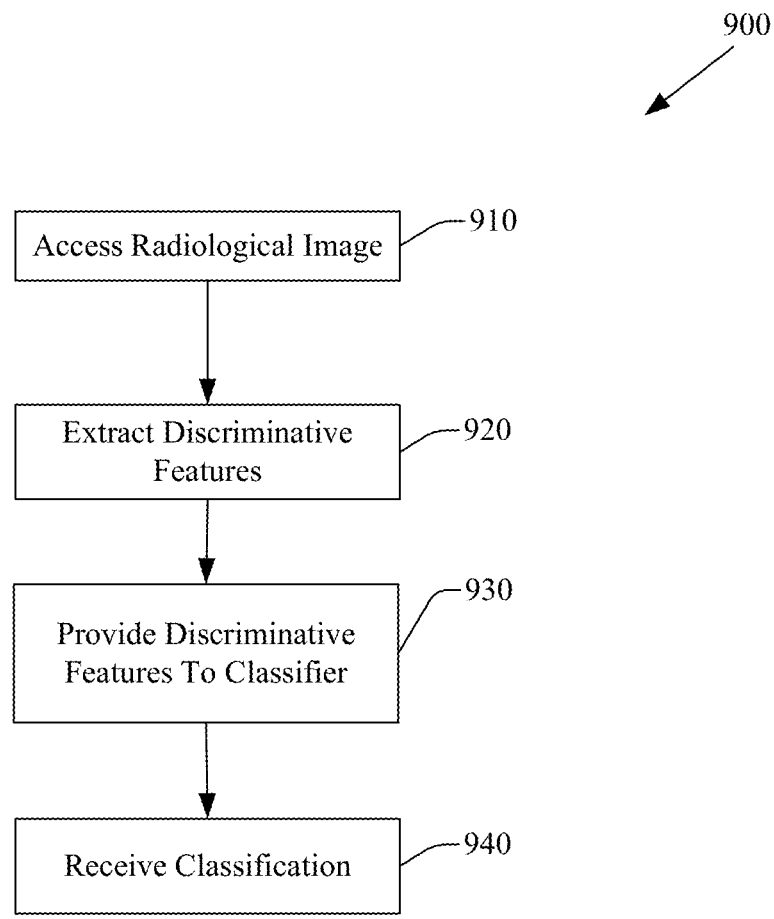
FIG. 9 illustrates an example method for predicting response to chemotherapy.

FIG. 9 illustrates an example method 900 for predicting response to chemotherapy. Method 900 includes, at 910, accessing a pre-treatment radiological image of a region of tissue demonstrating cancerous pathology. The radiological image includes a plurality of pixels. The radiological image further includes a segmented tumoral volume and a segmented peritumoral volume. The radiological image may be a CT image having a slice thickness.

Method 900 also includes, at 920, extracting a set of discriminative features from the tumoral volume and the peritumoral volume. In one embodiment, the set of discriminative features includes at least two features extracted from the tumoral volume and at least one feature extracted from the peritumoral volume. In one embodiment, the set of discriminative features includes a texture feature and a shape feature. In another embodiment, the set of discriminative features includes a mean of intratumoral sum average feature, a minimum of intratumoral Law feature, a sphericity feature, and a mean of peritumoral law feature.

Method 900 also includes, at 930, providing the set of discriminative features to a machine learning classifier. In one embodiment, the machine learning classifier is trained on an independent training set of images. The independent training set includes a pre-treatment image of a non-responder to chemotherapy, and a pre-treatment image of a responder to chemotherapy. In this embodiment, the machine learning classifier is tested on an independent validation set of images. The independent validation set includes a pre-treatment image of a non-responder to chemotherapy, and a pre-treatment image of a responder to chemotherapy. The independent training set and the independent validation set are disjoint sets. The machine learning classifier may be an LDA classifier, a QDA classifier, a KNN classifier, a random forest classifier, or an SVM classifier.

Method 900 further includes, at 940, receiving, from the machine learning classifier, a classification of the region of tissue. The region of tissue may be classified as a responder or as a non-responder. The classification is based, at least in part, on the set of discriminative features. The classification may include a probability that the region of tissue is a responder or non-responder.

Figure 10:
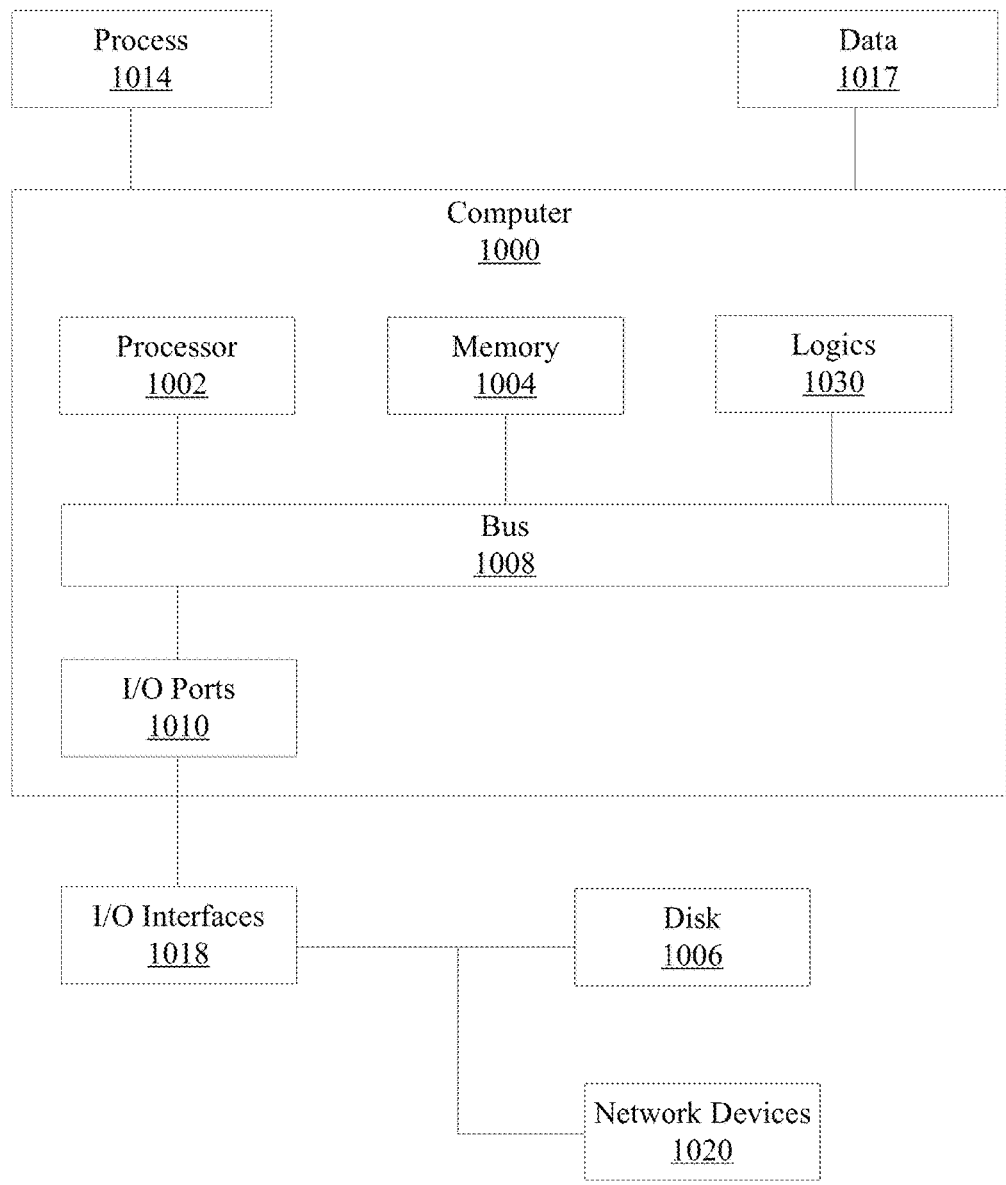
FIG. 10 illustrates an example computer in which example methods and apparatus may operate.

FIG. 10 illustrates an example computer 1000 in which example methods illustrated herein can operate and in which example circuits or logics may be implemented. In different examples, computer 1000 may be part of a digital whole slide scanner, may be operably connectable to a digital whole slide scanner system, or may be part of an automated tissue grading system, an automated cell counting system, or a CADx system.

Computer 1000 includes a processor 1002, a memory 1004, and input/output ports 1010 operably connected by a bus 1008. In one example, computer 1000 may include a set of logics 1030 that perform a method (e.g. method 100, method 200, method 300, method 900) of predicting response to pemetrexed chemotherapy. Thus, the set of logics 1030, whether implemented in computer 1000 as hardware, firmware, software, and/or a combination thereof may provide means (e.g., hardware, software) for predicting response to pemetrexed chemotherapy. In different examples, the set of logics 1030 may be permanently and/or removably attached to computer 1000. In one embodiment, the functionality associated with the set of logics 1030 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 1030 are implemented as ASICs or SOCs.

Processor 1002 can be a variety of various processors including dual microprocessor and other multi-processor architectures. Memory 1004 can include volatile memory and/or non-volatile memory. A disk 1006 may be operably connected to computer 1000 via, for example, an input/output interface (e.g., card, device) 1018 and an input/output port 1010. Disk 1006 may include, but is not limited to, devices like a magnetic disk drive, a tape drive, a Zip drive, a solid state device (SSD), a flash memory card, or a memory stick. Furthermore, disk 1006 may include optical drives like a CD-ROM or a digital video ROM drive (DVD ROM). Memory 1004 can store processes 1014 or data 1017, for example. Disk 1006 or memory 1004 can store an operating system that controls and allocates resources of computer 1000.

Bus 1008 can be a single internal bus interconnect architecture or other bus or mesh architectures. While a single bus is illustrated, it is to be appreciated that computer 1000 may communicate with various devices, logics, and peripherals using other busses that are not illustrated (e.g., PCIE, SATA, Infiniband, 1394, USB, Ethernet).

Computer 1000 may interact with input/output devices via I/O interfaces 1018 and input/output ports 1010. Input/output devices can include, but are not limited to, a CT system, digital whole slide scanners, an optical microscope, a keyboard, a microphone, a pointing and selection device, cameras, video cards, displays, disk 1006, network devices 1020, or other devices. Input/output ports 1010 can include but are not limited to, serial ports, parallel ports, or USB ports.

Computer 1000 may operate in a network environment and thus may be connected to network devices 1020 via I/O interfaces 1018 or I/O ports 1010. Through the network devices 1020, computer 1000 may interact with a network. Through the network, computer 1000 may be logically connected to remote computers. The networks with which computer 1000 may interact include, but are not limited to, a local area network (LAN), a wide area network (WAN), or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a solid state device (SSD), a memory stick, a data storage device, and other media from which a computer, a processor or other electronic device can read.

"Circuit", as used herein, includes but is not limited to hardware, firmware, software in execution on a machine, or combinations of each to perform a function(s) or an action(s), or to cause a function or action from another circuit, method, or system. Circuit may include a software controlled microprocessor, a discrete logic (e.g., ASIC), an analog circuit, a digital circuit, a programmed logic device, a memory device containing instructions, and other physical devices. Circuit may include one or more gates, combinations of gates, or other circuit components. Where multiple logical circuits are described, it may be possible to incorporate the multiple circuits into one physical logic or circuit. Similarly, where a single logical circuit is described, it may be possible to distribute that single circuit between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2 d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed by a computer control the computer to perform a method, the method comprising:
   accessing a pre-treatment radiological image of a region of tissue demonstrating cancerous pathology, where the radiological image includes a plurality of pixels, and where the radiological image includes an annotated region of interest (ROI) that defines a tumoral volume, where the tumoral volume includes a boundary;
   defining a peritumoral volume based on the boundary, where the peritumoral volume is defined based on the tumoral volume boundary and a number of pixels or a distance, where the number of pixels is determined heuristically;
   extracting a set of discriminative tumoral features from the tumoral volume;
   extracting a set of discriminative peritumoral features from the peritumoral volume;
   providing the set of discriminative tumoral features and the set of discriminative peritumoral features to a machine learning classifier;
   receiving, from the machine learning classifier, a classification of the region of tissue, where the classification is based on the set of discriminative tumoral features and the set of discriminative peritumoral features; and
   generating a personalized treatment plan based, at least in part, on the classification.

2. The non-transitory computer-readable storage device of claim 1, where the radiological image is a pre-treatment computed tomography (CT) image of a region of tissue demonstrating non-small cell lung cancer (NSCLC).

3. The non-transitory computer-readable storage device of claim 2, where the radiological image has a slice thickness, and where the set of discriminative tumoral features and the set of discriminative peritumoral features are selected based, at least in part, on the slice thickness.

4. The non-transitory computer-readable storage device of claim 1, where the number of pixels is seven, or where the distance is 2.5 mm to 5 mm.

5. The non-transitory computer-readable storage device of claim 1, the method further comprising training the machine learning classifier.

6. The non-transitory computer-readable storage device of claim 5, where training the machine learning classifier includes:
  accessing a training set of radiological images, where a member of the training set includes a plurality of pixels, and where the training set includes a pre-treatment radiological image of a region of tissue that responded to pemetrexed based chemotherapy, and a pre-treatment radiological image of a region of tissue that did not respond to pemetrexed based chemotherapy, where a member of the training set includes a set of features;
  annotating an ROI in the member of the training set, where the ROI defines a tumoral volume, where the tumoral volume includes a boundary;
  defining a peritumoral volume based on the boundary;
  selecting a first subset of candidate discriminative features from the tumoral volume;
  selecting a second, different subset of candidate discriminative features from the peritumoral volume, where the first subset of candidate discriminative features and the second, different subset of candidate discriminative features are selected using a T-Test approach, a Wilcoxon rank sum approach, a minimum redundancy maximum relevance (MRMR) approach, or a feed forward (FF) approach;
  providing the first subset of candidate discriminative features and the second, different subset of candidate discriminative features to the machine learning classifier;
  training the machine learning classifier with the first subset of candidate discriminative features and the second, different subset of candidate discriminative features; and
  testing the machine learning classifier.

7. The non-transitory computer-readable storage device of claim 6, where testing the machine learning classifier includes:
  accessing an independent validation set of radiological images, where a member of the independent validation set includes a plurality of pixels, and where the member of the independent validation set is a pre-treatment radiological image of a responder to pemetrexed based chemotherapy, or a pre-treatment radiological image of a non-responder to pemetrexed based chemotherapy;
  annotating a validation ROI in the member of the independent validation set, where the validation ROI defines a tumoral volume, where the tumoral volume includes a boundary;
  defining a peritumoral volume based on the boundary;
  extracting a first validation set of features from the tumoral volume;
  extracting a second validation set of features from the peritumoral volume, where the first validation set and the second validation set are based on the first subset of candidate discriminative features and the second, different subset of candidate discriminative features;
  providing the first validation set of features and the second validation set of features to the machine learning classifier; and
  receiving, from the machine learning classifier, a classification of the validation ROI, where the classification of the validation ROI is based, at least in part, on the first validation set of features and the second validation set of features.

8. The non-transitory computer-readable storage device of claim 1, where the set of discriminative tumoral features includes a shape feature and a texture feature.

9. The non-transitory computer-readable storage device of claim 8, where the set of discriminative tumoral features includes a sphericity feature, a Gabor feature, and a Law-Laplace feature.

10. The non-transitory computer-readable storage device of claim 1, where the set of discriminative peritumoral features includes a texture feature.

11. The non-transitory computer-readable storage device of claim 10, where the set of discriminative peritumoral features includes a mean of Law feature.

12. The non-transitory computer-readable storage device of claim 1, where the machine learning classifier is a linear discriminant analysis (LDA) classifier, a quadratic discriminant analysis (QDA) classifier, a K-nearest neighbors (KNN) classifier, a random forest (RF) classifier, or a support vector machine (SVM) classifier.

13. An apparatus for predicting response to pemetrexed therapy in non-small cell lung cancer (NSCLC) patients, comprising:
  a processor;
  a memory;
  an input/output interface;
  a set of circuits; and
  an interface to connect the processor, the memory, the input/output interface and the set of circuits, where the set of circuits includes:
    an image acquisition circuit that acquires a radiological image of a region of tissue demonstrating NSCLC, where the radiological image includes a plurality of pixels, and where the radiological image includes a region of interest (ROI) that defines a tumoral volume, where the ROI has a boundary;
    a peritumoral volume definition circuit that defines a peritumoral volume based, at least in part, on the boundary of the ROI and a distance, where the distance is a number of pixels, and where the distance is heuristically determined;
    a feature extraction circuit that extracts a set of discriminative tumoral features from the tumoral volume, and a set of discriminative peritumoral features from the peritumoral volume; and
    a classification circuit that classifies the ROI as a responder or a non-responder using a machine learning classifier based, at least in part, on the set of discriminative tumoral features and the set of discriminative peritumoral features.

14. The apparatus of claim 13, where the radiological image is a computed tomography (CT) image, and where the radiological image has a slice thickness.

15. The apparatus of claim 14, where the feature extraction circuit extracts the set of discriminative tumoral features and the set of discriminative peritumoral features based, at least in part, on the slice thickness, where the set of discriminative tumoral features includes a shape feature and a texture feature, and where the set of discriminative peritumoral features includes a texture feature.

16. The apparatus of claim 15, where the classification circuit classifies the ROI using a linear discriminant analysis (LDA) machine learning classifier, or where the classification circuit classifies the ROI using a machine learning classifier selected from at least one of an LDA, a quadratic discriminant analysis (QDA) classifier, a K-nearest neighbors (KNN) classifier, a random forest classifier, or a support vector machine (SVM) classifier based, at least in part, on the slice thickness.

17. The apparatus of claim 16, the set of circuits further comprising a training circuit that trains the machine learning classifier using an independent learning set of radiological images and an independent testing set of radiological images.

* * * * *